(12) United States Patent
Behnam (10) Patent No.: US 12,144,784 B2
(45) Date of Patent: Nov. 19, 2024

(54) SOLUBILIZATE WITH CURCUMIN AND OPTIONALLY AT LEAST ONE OTHER ACTIVE SUBSTANCE

(71) Applicant: Aquanova AG, Darmstadt (DE)

(72) Inventor: Dariush Behnam, Rossdorf (DE)

(73) Assignee: Aquanova AG, Darmstadt (DE)

(*) Notice: Subject to any disclaimer, the term of this patent is extended or adjusted under 35 U.S.C. 154(b) by 0 days.

(21) Appl. No.: 18/600,907

(22) Filed: Mar. 11, 2024

(65) Prior Publication Data

US 2024/0216297 A1 Jul. 4, 2024

Related U.S. Application Data

(62) Division of application No. 17/544,808, filed on Dec. 7, 2021, now Pat. No. 11,931,322, which is a division
(Continued)

(30) Foreign Application Priority Data

| Jul. 11, 2017 | (DE) | 10 2017 115 496.5 |
| Jul. 11, 2017 | (WO) | PCT/EP2017/067381 |
| Jul. 11, 2017 | (WO) | PCT/EP2017/067382 |

(51) Int. Cl.
*C07C 39/21* (2006.01)
*A61K 9/107* (2006.01)
(Continued)

(52) U.S. Cl.
CPC ............ *A61K 31/12* (2013.01); *A61K 9/107* (2013.01); *A61K 9/1075* (2013.01); *A61K 9/48* (2013.01);
(Continued)

(58) Field of Classification Search
CPC ..................................................... C07C 39/21
See application file for complete search history.

(56) References Cited

U.S. PATENT DOCUMENTS 5,629,351 A 5/1997 Taneja et al.
5,972,382 A 10/1999 Majeed et al.
(Continued)

FOREIGN PATENT DOCUMENTS

CN 104720070 A 6/2015
CN 103861090 B 6/2017
(Continued)

OTHER PUBLICATIONS

Alexa Kocher et al, "The oral bioavailability of curcuminoids in healthy humans is markedly enhanced by micellar solubilisation but not further improved by simultaneous ingestion of sesamin, ferulic acid, naringenin and xanthohumol", Journal of Functional Foods, vol. 14, Apr. 1, 2015 (Apr. 1, 2015), p. 183-191.
(Continued)

*Primary Examiner* — Rosanne Kosson
(74) *Attorney, Agent, or Firm* — Smartpat PLC (57) ABSTRACT

In order to make available the health-promoting and healing properties of curcumin to the human or animal organism, also in combination with at least one further active substance, a solubilizate consists of or contains a content of curcumin equal to or smaller than 10 wt %, preferably equal to or smaller than 7.5 wt %, most preferably 6 wt %, and at least one emulsifier with an HLB value in a range below 18, preferably between 13 and 18, namely polysorbate 80 or polysorbate 20 or a mixture of polysorbate 20 and polysorbate 80, with an average diameter of the curcumin-loaded micelles ranging from 5 nm to 40 nm, preferably from 6 nm to 20 nm, most preferably from 7 nm to 10 nm, for use in particular as a dietary supplement and/or pharmaceutical
(Continued)

drug for treating and/or preventing diseases involving inflammation, cancer and other diseases.

6 Claims, 4 Drawing Sheets

Related U.S. Application Data of application No. 16/629,155, filed as application No. PCT/EP2018/068731 on Jul. 11, 2018, now Pat. No. 11,197,834.

(51) Int. Cl.
| | |
|---|---|
| A61K 9/48 | (2006.01) |
| A61K 31/05 | (2006.01) |
| A61K 31/12 | (2006.01) |
| A61K 31/122 | (2006.01) |
| A61K 31/19 | (2006.01) |
| A61K 31/352 | (2006.01) |
| A61K 36/324 | (2006.01) |
| A61K 38/48 | (2006.01) |
| A61K 47/10 | (2017.01) |
| A61K 47/26 | (2006.01) |

(52) U.S. Cl.
CPC ............ *A61K 9/4825* (2013.01); *A61K 31/05* (2013.01); *A61K 31/122* (2013.01); *A61K 31/19* (2013.01); *A61K 31/352* (2013.01); *A61K 36/324* (2013.01); *A61K 38/4886* (2013.01); *A61K 47/10* (2013.01); *A61K 47/26* (2013.01)

(56) References Cited

U.S. PATENT DOCUMENTS

| | | | |
|---|---|---|---|
| 7,682,636 | B2 | 3/2010 | Babish et al. |
| 8,808,734 | B2 | 8/2014 | Winnicki |
| 11,197,834 | B2 | 12/2021 | Behnam |
| 11,344,509 | B2 | 5/2022 | Behnam |
| 11,786,484 | B2 | 10/2023 | Behnam |
| 2004/0138293 | A1 | 7/2004 | Werner et al. |
| 2005/0129791 | A1 | 6/2005 | Babish et al. |
| 2007/0104741 | A1 | 5/2007 | Murty et al. |
| 2008/0220102 | A1 | 9/2008 | Behnam |
| 2009/0087419 | A1 | 4/2009 | Sakai et al. |
| 2009/0208472 | A1 | 8/2009 | Sakai et al. |
| 2010/0029757 | A1 | 2/2010 | Hellerbrand |
| 2010/0098676 | A1 | 4/2010 | Gokaraju et al. |
| 2011/0086017 | A1 | 4/2011 | Kravets et al. |
| 2011/0129546 | A1 | 6/2011 | Mill |
| 2011/0207697 | A1 | 8/2011 | Ono et al. |
| 2011/0293678 | A1 | 12/2011 | Behnam |
| 2015/0342881 | A1 | 12/2015 | Behnam |
| 2016/0008298 | A1 | 1/2016 | Stevens |
| 2016/0022569 | A1 | 1/2016 | Tonge et al. |
| 2016/0074316 | A1 | 3/2016 | Caetano et al. |
| 2016/0081975 | A1 | 3/2016 | Bromley |
| 2017/0042835 | A1 | 2/2017 | Singh |
| 2017/0333515 | A1* | 11/2017 | Kuhrts ............... A23L 2/52 |
| 2018/0280464 | A1 | 10/2018 | Martin |
| 2019/0314326 | A1 | 10/2019 | Garti et al. |
| 2019/0365667 | A1 | 12/2019 | Wright et al. |
| 2020/0129452 | A1 | 4/2020 | Behnam |
| 2020/0222346 | A1 | 7/2020 | Behnam |
| 2022/0133646 | A1 | 5/2022 | Behnam |
| 2022/0133682 | A1 | 5/2022 | Behnam |
| 2022/0202713 | A1 | 6/2022 | Behnam |

FOREIGN PATENT DOCUMENTS

| | | |
|---|---|---|
| CN | 106619588 B | 8/2019 |
| DE | 102006024911 A1 | 11/2007 |
| DE | 102006062264 A1 | 6/2008 |
| DE | 202012012130 U1 | 3/2014 |
| EP | 0755940 A1 | 1/1997 |
| EP | 1431385 A1 | 6/2004 |
| EP | 2018869 A1 | 1/2009 |
| JP | H07165588 A | 6/1995 |
| JP | H11500725 A | 1/1999 |
| JP | 2005179213 A | 7/2005 |
| JP | 2009514890 A | 4/2009 |
| JP | 2011524884 A | 9/2011 |
| JP | 2016505579 A | 2/2016 |
| JP | 2017178866 | 10/2017 |
| RU | 2530056 C2 | 10/2014 |
| WO | 03092664 A1 | 11/2003 |
| WO | 2005092352 A1 | 10/2005 |
| WO | 2007006497 A2 | 1/2007 |
| WO | 2007058480 A1 | 5/2007 |
| WO | 2008065451 A2 | 6/2008 |
| WO | 2012093524 A1 | 7/2012 |
| WO | 2014094921 A1 | 6/2014 |
| WO | 2015171445 A1 | 11/2015 |
| WO | 2016022936 A1 | 2/2016 |
| WO | 2018061007 A1 | 4/2018 |
| WO | 2019011415 A1 | 1/2019 |

OTHER PUBLICATIONS

Bhagat Shivani, Agarwal Monika, Roy Vandana, "Serratiopeptidase: a systematic review of the existing evidence", International Journal of Surgery, Feb. 1, 2013, Surgical Associates, London, GB, Source info: vol. 11, Nr: 3, pp. 209-217.

Christina Schiborr, Alexa Kocher, Dariush Behnam, Josef Jandasek, Simone Toelstede, Jan Frank, "The oral bioavailability of curcumin from micronized powder and liquid micelles is significantly increased in healthy humans and differs between sexes", Molecular Nutrition & Food Research ,Mar. 1, 2014, Wiley—VCH Verlag, Weinheim, Germany, vol. 58, Nr: 3, pp. 516-527.

Dorn et al., "Increased expression of c-Jun in nonalcoholic fatty liver disease", Lab Invest., (20140000), vol. 94, pp. 394-408.

Edward Lau (deceased), Chapters, Preformulation Studies pp. 173-234, of "Handbook of Modern Pharmaceutical Analysis", by Academic Press, Edited by Satinder Ahuja and Stephen Scypinski, (2001), vol. 3, pp. 1-566. (Year: 2001).

F. Capasso et al., "Glycyrrhetinic acid, leucocytes and prostaglandins", J. Pharm. Pharmacol. 1983, 35: 332-335.

Hellebrand et al., "Promoterhypermethylation is causing functional relevant downregulation of methylthioadenosine phosphorylase (MTAP) expression in hepatocellular carcinoma", Carcinogenesis, (20060000), vol. 27, pp. 64-72.

K. Gerbeth et al., "Determination of major boswelic acids in plasma by high-pressure liquid chromatography/mass spektrometry", Journal of Pharmaceutical and Biomedical Analysis, vol. 56, No. 5, pp. 998-1005.

Kerstin Gross-Steinmeyer, Patricia L Stapleton, Julia H Tracy, Theo K Bammler, Stephen C Strom, Donald R Buhler, David L Eaton, "Modulation of Aflatoxin B1-Mediated Genotoxicity in Primary Cultures of Human Hepatocytes by Diindolylmethane, Curcumin, and Xanthohumols", Toxicological Sciences,,Dec. 1, 2009,Academic Press, vol. 112, Nr: 2, pp. 303-310.

Khayyal M T, "Novel formulations of Curcumin, Boswellia and Xanthohumol extracts markedly enhance their individual and combined anti-inflammatory activity", EMBASE01 Sep. 2017 (Sep. 1, 2017), Database accession No. EMB-621379886, Retrieved from the Internet: URL:Elsevier Science Publishers, Amsterdam, NL, XP002783955, 1-20 the whole document & Zeitschrift Fur Phytotherapie Sep. 1, 2017 Hippokrates Verlag GMBH NLD, vol. 38, No. Supplement 1, Sep. 1, 2017 (Sep. 1, 2017).

Lini Alappat, Atif B Awad, "Curcumin and obesity: evidence and mechanisms", Nutrition Reviews,,Dec. 1, 2010, International Life Sciences Institute, vol. 68, Nr: 12, pp. 729-738.

Liu, Chen et al., "Enhanced skin permeation of glabridin using eutectic mixture-based nanoemulsion", Drug Deliv. Transl. Res., 2017, vol. 7, pp. 325-332.

(56) References Cited

OTHER PUBLICATIONS

Manju Rawat Singh, Singh Deependra, Swarnlata Saraf, "Development and in vitro evaluation of polar lipid based lipospheres for oral delivery of peptide drugs", International Journal of Drug Delivery,,Jul. 31, 2009, vol. 1, Nr: 1, pp. 15-26.

Manju Rawat, Swarnlata Saraf, "Formulation optimization of double emulsification method for preparation of enzyme-loaded Eudragit S100 microspheres", Journal of Microencapsulation, Jun. 1, 2009, Taylor And Francis, Basingstoke, GB, vol. 26, Nr: 4, pp. 306-314.

Pearson, "Development of Arthritis, Periarthritis and Periostitis in Rats Given Adjuvants". Proceedings of the Society for Experimental Biology and Medicine, vol. 91 issue: 1, pp. 95-101Issue published: Jan. 1, 1956.

Peshkovsky (Alexy Peshkovsky, Ph.D. Sonomecahnics Blog, Jul. 3, 2016, 6 pages of PDF). (Year: 2016).

Raju Gautam, Sanjay M Jachak, "Recent developments in antiinflammatory natural products", Publication data: Medicinal Research Reviews, Sep. 1. 2009, New York, NY, US, Source info: vol. 29, Nr: 5, pp. 767-820.

Rawat, Manju, Shailendra Saraf, and Swarnlata Saraf. "Influence of selected formulation variables on the preparation of enzymeentrapped Eudragit S100 microspheres." AAPS pharmscitech 8 (2007): 289-297.

Reji Kizhakkedath, "Clinical evaluation of a formulation containing Curcuma longa and Boswellia serrata extracts in the management of knee osteoarthritis", Molecular Medicine Reports, vol. 8, No. 5, Nov. 1, 2013 (Nov. 1, 2013), p. 1542-1548.

Rosenkrantz, Harris, George R. Thompson, and Monique C. Braude. "Oral and parenteral formulations of marijuana constituents." Journal of Pharmaceutical Sciences 61, No. 7 (1972): 1106-1112.

Tominaga et al.: "Licorice flavonoid oil effects body weight loss by reduction of body fat mass in overweight subjects", Journal of Health Science 52(6), 2006, pp. 672-683.

Tominaga et al.: "Licorice flavonoid oil reduced total body fat and visceral fat in overweight subjects: a randomized, double-blind, placebo-controlled study", Obesity Research & Clinical Practice (3), 2009, pp. 169-178.

U. Siemoneit et al., "Inhibition of microsomal prostaglandin E-synthase-1 as a molecular basis for the antiinflammatory actions of boswellic acids from frankincense", British Journal of Pharmacology, vol. 162, No. 1, pp. 147-162.

Wobser et al., "Lipid accumulation in hepatocytes induces fibrogenic activation of hepatic stellate cells", Cell Res, (20090000), vol. 19, pp. 996-1005.

Zamzow Daniel R et al, "Xanthohumol improved cognitive flexibility in young mice", Behavioural Brain Research, vol. 275, Sep. 1, 2014 (Sep. 1, 2014), p. 1-10.

Zeitschrift Fur Phytotherapie Sep. 1, 2017 Hippokrates Verlag GMBH NLD, Sep. 1, 2017, vol. 38, Supplement 1, ISSN 1438-9584, Abstract.

\* cited by examiner

SOLUBILIZATE WITH CURCUMIN AND OPTIONALLY AT LEAST ONE OTHER ACTIVE SUBSTANCE

TECHNICAL FIELD

The disclosure relates to a solubilizate comprising curcumin and optionally at least one further active substance. Furthermore, the disclosure relates to a fluid containing such a solubilizate, to a capsule filled with such a solubilizate or fluid, and to a dietary supplement and/or pharmaceutical drug containing such a solubilizate.

BACKGROUND

Curcumin is discussed as an active substance based on various potential pharmacological properties. For example, there are indications for the antioxidant and also for the anti-inflammatory effect of curcumin as well as for the effectiveness against viruses and bacteria as well as against cancer. Indications could therefore be, for example, Parkinson's, Alzheimer's, diabetes, colorectal tumors, pancreatic cancer, and liver dysfunction.

In order to be able to enter the bloodstream after oral intake, the active substance must pass through the small intestinal blood barrier, is then metabolized in the liver and enters the hepatic vein as a bioavailable fraction. The rest of the total active substance ingested and released in the body is either degraded microbially in the intestine or eliminated with the faeces or bile.

The inventor has already created a curcumin solubilizate which has significantly increased bioavailability compared to native curcumin. This solubilizate is described in international patent application WO 2014094921 A1. Surprisingly, it has been found in several studies that in addition to its high bioavailability, this curcumin solubilizate in its specific formulation also has an unexpectedly greater effect on the reduction of disease symptoms which are in particular associated with inflammation or cancer.

A toxicity due to the micellization of the active substance according to the disclosure in comparison to the native form could be ruled out on the basis of studies with MTT assays for cell viability. The verification of cell vitality by MTT assay is based on the reduction of the yellow water-soluble dye 3-(4,5-dimethylthiazol-2-yl)-2,5-diphenyltetrazolium bromide (MTT) into a blue-violet water-insoluble formazan.

SUMMARY

The inventor has therefore set itself the task of providing a formulation which makes the health-promoting or curative properties of curcumin available for the human or animal organism, also in view of a combination with at least one further active substance. In particular, it is an object of the disclosure to provide a highest possible bioavailability of curcumin in combination with at least one further active substance.

These objects are achieved in a surprisingly simple way with a solubilizate as claimed. This solubilizate consists of or contains curcumin in a content of less than or equal to 10 wt %, preferably less than or equal to 7.5 wt %, most preferably 6 wt %, and at least one emulsifier having an HLB value in the range between 13 and 18, namely polysorbate 80 or polysorbate 20 or a mixture of polysorbate 20 and polysorbate 80, wherein the average diameter of the curcumin-loaded micelles is between 5 nm and 40 nm, preferably between 6 nm and 20 nm, most preferably between 7 nm and 10 nm, for use in particular as a pharmaceutical drug in the treatment and/or prevention of diseases involving inflammation, cancer, Alzheimer's, Parkinson's, obesity, high cholesterol, elevated blood sugar, diabetes, metabolic syndrome, and/or autoimmune diseases, multiple sclerosis (MS), for reducing visceral fat, for thermogenesis, for lowering cholesterol, in particular LDL cholesterol, and/or glucose in the blood and/or triglycerides in the blood, for improving macular pigment density, for reducing oxidative stress and/or for reducing the accumulation of fat in the hepatocytes, in particular as a pharmaceutical drug for treating and/or preventing fatty liver disease, Friedreich's ataxia, lysosomal diseases, in particular Tay-Sachs disease, arteriosclerosis, heart diseases, arthritis.

The inventor has moreover found that the positive effect of curcumin on healing processes or maintenance of health can surprisingly be exploited synergistically, at least partially, in combination with other active substances. In an advantageous embodiment, the disclosure provides a solubilizate consisting of or containing curcumin in a content of less than or equal to 10 wt %, preferably less than or equal to 8 wt %, most preferably 3 wt % to 7 wt %; and at least one further active substance; and at least one emulsifier having an HLB value in a range below 18, preferably between 13 and 18, in particular polysorbate 80 or polysorbate 20 or a mixture of polysorbate 20 and polysorbate 80.

In an advantageous embodiment, the solubilizate is provided in a form that can be administered orally, in particular in a curcumin dose in the range from 0.5 mg/kg body weight to 1 mg/kg body weight, preferably in a dose of 0.81 mg/kg body weight, in particular once a day.

For the purposes of this application, the term "active substance" refers to a substance that is provided in a pharmaceutically effective concentration and is preferably added for the purpose of having a pharmaceutical effect. Here, the name of the respective active substance is understood to encompass also substances that are converted in the body into the active substance and/or into its biologically active form.

For the purposes of this application, these "active substances" include secondary phytochemicals which are produced as chemical compounds by plants, neither in energy metabolism nor in anabolic or catabolic metabolism. One group of secondary phytochemicals and thus active substances in the sense of the present application are flavonoids. The active substances in the sense of the present application also include natural polyphenols such as resveratrol or the polyphenols from licorice, and natural phenols, in particular chalcones such as xanthohumol and also include plant extracts, i.e. substances that were extracted from plants or parts of plants using an extractant. These include extracts from hops or from the root material of the licorice plant. The active substance is referred to as an "extract" even if it is still dissolved in the extractant.

The active substances in the sense of the present application also include enzymes. One example of an enzyme as an active substance in the present application is serrapeptase. However, the application is not limited to this enzyme.

The extract from the resin of the frankincense tree, *Boswellia serrata* extract, contains several pentacyclic triterpenes which together are often referred to as total boswellic acids ("total BAs"). The term "boswellic acids" refers to a group of chemical compounds naturally occurring in the resin of the frankincense trees mentioned above. The two basic structures are α-boswellic acid and β-boswellic acid. Also, some derivatives of the boswellic acids are known, in particular compounds which carry a keto group at position 11 and/or which are acetylated at position 3. Boswellic acids that are currently considered to be significant in terms of pharmacological effects in particular include α-boswellic acid (αBA) and β-boswellic acid (BBA) and their derivatives 11-keto-β-boswellic acid (KBA); CAS 17019-92-0) and 3-O-acetyl-11-keto-β-boswellic acid (AKBA); CAS 67416-16-9), and 3-O-acetyl-α-boswellic acid (AαBA), and 3-O-acetyl-β-boswellic acid (ABBA). In particular the derivative AKBA is considered to have an anti-inflammatory effect.

In the context of the present application, the term "Boswellia", in particular in the term "Boswellia solubilizate" is used in the sense that the term "Boswellia" refers to the active substances from the resin of the frankincense tree, i.e. to at least one boswellic acid and/or at least one derivative of a boswellic acid. The term "boswellic acid solubilizate" refers to a micellar formulation of at least one boswellic acid which may also contain at least one boswellic acid derivative.

Xanthohumol is a flavonoid naturally occurring in hops. It is a prenylated plant polyphenol which is assigned to the chalcones and has only been identified in hops so far. The bitter hop varieties have a significantly higher content of xanthohumol than aroma varieties. In tests, xanthohumol was found to be effective against the emergence and development of cancer cells. In laboratory experiments, it was moreover found that xanthohumol is capable of protecting the nerve cells of the brain and thus could possibly help to slow down the course of diseases like Alzheimer's or Parkinson's.

Licorice flavonoid oil (LFO) consisting of hydrophobe licorice polyphenols in medium-chain triglycerides has a weight-reducing effect that is associated with reduced body fat. Moreover, antioxidant properties are attributed to ethanolic extracts of licorice. Licorice flavonoid oil with a glabridin concentration of 3% has the brand name "KANEKA GLAVONOID™". It will also be referred to as "glavonoid" below.

Resveratrol is a phytoalexin with antioxidant properties, belonging to the polyphenols. The substance is found in grapes, for example, in the skin of red grapes even in relatively large quantities, but also in raspberries, mulberries, plums, peanuts, and Japanese Knotweed. Resveratrol can also be isolated from the grapevine itself. According to the entry in the online encyclopedia Wikipedia, in vitro studies have shown evidence of potential anticancer activity and beneficial effects in diseases such as atherosclerosis, heart diseases, Alzheimer's disease, arthritis, and some autoimmune diseases.

Serratia peptidase or serrapeptase is a proteolytic enzyme produced by the bacterium Serratia which lives in the intestine of the silkworm. Serrapeptase is said to have beneficial effects in relieving pain, inflammation, traumatic swelling, and excess mucus secretion by the organism. It is said to be effective like an anti-inflammatory and analgesic similar to acetylsalicylic acid, ibuprofen or other non-steroidal analgesics. It is also said to induce fibrinolytic anti-inflammatory and anti-oedematous activity in the tissue. Like all enzymes, serrapeptase is sensitive to the acids produced by the stomach. Therefore, the provision in a formulation that allows gastric passage is an object of the disclosure.

The solubilizate according to the disclosure may contain one or more boswellic acids and/or one or more boswellic acid derivatives in a content of less than or equal to 10 wt %, preferably less than or equal to 8 wt %, most preferably 4.7 wt % to 6.6 wt %.

Due to the high proportion of Boswellia, the disclosure contemplates, in an advantageous embodiment thereof, that the solubilizate contains an extract obtained from the resin of the plant Boswellia serrata by extraction using ethyl acetate, as a source of the one or more boswellic acids and/or one or more boswellic acid derivatives, with boswellic acids being contained in a concentration of at least 85 wt % in this extract.

The solubilizate according to the disclosure may contain xanthohumol in an amount of less than or equal to 10 wt %, preferably less than or equal to 5 wt %, most preferably 1 wt % to 3 wt %.

Due to the high proportion of xanthohumol, the disclosure contemplates, in an advantageous embodiment thereof, that the solubilizate contains an ethanolic extract of hard resins from hops as a source of xanthohumol, with a xanthohumol concentration in this extract in a range between 65 wt % and 95 wt %, preferably in a concentration in a range from 80% to 92 wt %. In particular the products "Xantho-Flav Pure" or "Xantho-Flav" that will be discussed in more detail below can be used as a xanthohumol source in the context of the disclosure.

The solubilizate according to the disclosure may contain a fluid containing licorice root extract, in particular a hydrophobic solution of a licorice root extract, preferably glavonoid, and/or glabridin, in an amount of less than or equal to 35 wt %, preferably less than or equal to 20 wt %, most preferably from 0.3 wt % to 17 wt %.

The solubilizate according to the disclosure may contain resveratrol in a range between 1 wt % and 15 wt %, most preferably in a range between 5 wt % and 10 wt %.

The solubilizate according to the disclosure may contain serrapeptase in a range of up to 3 wt %, preferably in a range between 0.1 wt % and 2 wt %, most preferably in a range between 0.18 wt % and 0.35 wt %.

The solubilizate according to the disclosure may contain coenzyme $Q_{10}$ in a range of up to 10 wt %, preferably in a range between 0.1 wt % and 5 wt %, most preferably in a range between 0.5 wt % and 1.5 wt %.

The solubilizate according to the disclosure may contain α-liponic acid in a range of up to 10 wt %, preferably in a range between 0.1 wt % and 5 wt %, most preferably in a range between 0.8 wt % and 2.5 wt %.

A solubilizate consisting of or containing curcumin and at least one further active substance may also be provided or employed advantageously within the context of the disclosure for use as an antibiotic and/or as a pharmaceutical drug in the treatment and/or prevention of diseases involving inflammation, cancer, Alzheimer's, Parkinson's, obesity, high cholesterol, elevated blood sugar, diabetes, metabolic syndrome, and/or autoimmune diseases, multiple sclerosis (MS), for reducing visceral fat, for thermogenesis, for lowering cholesterol, in particular LDL cholesterol, and/or glucose in the blood and/or triglycerides in the blood, for improving macular pigment density, for reducing oxidative stress and/or for reducing the accumulation of fat in the hepatocytes, in particular as a pharmaceutical drug for treating and/or preventing fatty liver disease, Friedreich's ataxia, lysosomal diseases, in particular Tay-Sachs disease, arteriosclerosis, heart diseases, arthritis.

In particular, the disclosure provides the solubilizates as described above for use as an anti-inflammatory drug and/or as an antibiotic and/or as a pharmaceutical drug with an effect against cancer, Alzheimer's, Parkinson's, obesity, high cholesterol, elevated blood sugar, diabetes, metabolic syndrome, and/or autoimmune diseases, multiple sclerosis (MS), for lowering visceral fat, for thermogenesis, as a cholesterol-lowering pharmaceutical drug, in particular with respect to LDL cholesterol, and/or as a pharmaceutical drug with an effect for lowering glucose in the blood and/or triglycerides in the blood, for improving macular pigment density, for reducing oxidative stress and/or for reducing the accumulation of fat in the hepatocytes, in particular as a pharmaceutical drug with an effect against fatty liver, Friedreich's ataxia, lysosomal diseases, in particular Tay-Sachs disease, arteriosclerosis, heart diseases, arthritis.

It has also proved to be advantageous in this context for the solubilizate according to the disclosure that the total curcuminoid concentration in human blood plasma measured one hour after oral administration of 500 mg of curcumin in the form of the solubilizate as described above is about 500 ng curcuminoid per mL plasma ±100 ng curcuminoid per mL plasma. The total curcuminoid concentration in human blood plasma measured over a period of 24 hours as the area under the total curcumin plasma concentration vs. time curve (AUC) is in the range from about 9,500 to about 10,000 nmol·h/L. Thus, the solubilizate is available to the body to a great extent even after oral administration.

The disclosure advantageously provides solubilizates with very good anti-inflammatory properties. The anti-inflammatory activity measured as the concentration of C-reactive protein (CRP) in the blood serum of arthritic rats after a single administration of the solubilizate according to the disclosure in a dose of 5 mg/kg body weight of curcumin is in the range from about 2100 pg/mL to about 2500 pg/mL, and after a single administration of the solubilizate in a dose of 10 mg/kg body weight of curcumin it is in the range from about 1400 pg/mL to about 1800 pg/mL.

The anti-inflammatory effect measured as the concentration of myeloperoxidase (MPO) in the blood serum of arthritic rats after a single administration of the solubilizate in a dose of 5 mg/kg body weight of curcumin is in the range from about 800 mU/mL to about 900 mU/mL. These values are significantly lower than those for native curcumin, as will be explained in more detail below.

The anti-inflammatory activity of an inventive solubilizate comprising curcumin and *Boswellia* measured as the concentration of C-reactive protein (CRP) in the blood serum of arthritic rats after a single administration of the solubilizate in a dose of 5 mg/kg body weight of curcumin and 10 mg/kg body weight of boswellic acids is in a range from about 1200 pg/mL to about 1500 pg/mL, compared to between about 3200 pg/mL and about 3500 pg/mL after administration of the same dose of native curcumin and *Boswellia*, respectively.

The anti-inflammatory effect of an inventive solubilizate comprising curcumin and *Boswellia*, measured as the concentration of myeloperoxidase (MPO) in the blood serum of arthritic rats after a single administration of the solubilizate in a dose of 5 mg/kg body weight of curcumin and 10 mg/kg body weight of boswellic acids is in a range from about 750 mU/mL to about 815 mU/mL and thus is significantly lower than the about 1150 mU/mL to about 1250 mU/mL after administration of the same dose of native curcumin and *Boswellia*, respectively.

The enzyme unit (U) is a unit which has since been replaced by the katal (kat) to indicate enzymatic activity. Since the numerical values change when katal is used, the enzyme unit (U) continues to be used in medicine and clinical chemistry. One enzyme unit U corresponds to one micro-mole substrate conversion per minute.

Furthermore, the disclosure offers the advantage of providing the solubilizate according to the disclosure for use in agriculture, fish farming and/or horticulture and/or in the field of food hygiene and/or for use as a disinfectant and/or in the field of packaging, preferably in the packaging of beef, poultry or fish, and/or for use as a disinfectant.

In particular for the solubilizate with curcumin as the only active substance it was possible to show that in terms of germ contamination of foods the treatment with the solubilizate according to the disclosure resulted in a significant reduction of the microbial load. The curcumin is effective as a photosensitizer in this case. It is applied locally to a surface infected by microbes and absorbed by the microbes there, and then the surface is exposed to light whereby the photosensitizer is activated, which then produces reactive oxygen species ("oxygen radicals") in the microbes which are killed thereby.

In the food sector, for example in antimicrobial packaging, the food such as meat can be sprayed with an aqueous solution of a solubilizate according to the disclosure and packed in transparent films made of PP, PE, PC or the like and then exposed to light, so as to keep the surface of already packaged food germ-free. Corresponding applications for germ-free packaging of other items are also within the scope of the disclosure. This includes, for example, the packaging of surgical instruments and similar utensils.

The advantage of the formulation as a solubilizate according to the disclosure for this type of application is that the active substance, in particular the curcumin, can be used in a very high aqueous dilution, so that a color load of the treated surface can be substantially completely excluded. Due to the high number of very small micelles, uniform and sufficient distribution of the active substance of the solubilizate is achieved on the surface to be treated even with strong dilution. This allows for application of the disclosure in the field of the most germ-free possible packaging by way of example, in a simple and very cost-effective way.

In order to provide stable micelles of the active substances, the emulsifier content, in particular the polysorbate content, may be at least 70 wt %, preferably in the range between 75 wt % and 95 wt %, most preferably in the range between 79 wt % and 88 wt % within the context of the disclosure, depending on the further components that are contained in the solubilizate.

Depending on the specific application, the solubilizate of the disclosure may contain up to 20 wt %, preferably up to 15 wt % of ethanol, for example, and/or up to 25 wt %, preferably between 12 wt % and 20 wt %, most preferably up to 10 wt % of glycerol, and/or additionally up to 10 wt %, preferably up to 7 wt % of water. With the addition of ethanol, the content of polysorbate can be reduced, which is an advantage in view of the ADI value for polysorbate (25 mg/kg body weight), recommended by WHO. The content of polysorbate may also be reduced by adding glycerol.

The solubilizates of the disclosure exhibit a narrow particle size distribution with small mean particle size, even under the physiological conditions of a gastric passage; the distribution of the diameter of the micelles in a dilution of the solubilizate with distilled water in a ratio of 1:500 at pH 1.1 and 37° C. ranges from about $d_{10}$=6 nm to about $d_{90}$=20 nm. These values were determined from a volume distribution. Details of particle size analysis of the micelles of the solubilizates will be discussed below.

An indication of the improved bioavailability compared to compositions of curcumin or of curcumin and at least one further active substance that have not been micellated according to the disclosure is obtained by a measurement of turbidity of the solubilizate, which is much easier accessible to measurement techniques. As a result of the formulation according to the disclosure, the turbidity of the solubilizate is preferably less than 25 FNU, more preferably less than 3 FNU, measured by scattered light measurement using infrared light according to the specifications of the ISO 7027 standard at a dilution of the solubilizate in a ratio of 1:50 or 1:500 in water under physiological conditions (pH 1.1 and 37° C.).

In order to facilitate oral application of the solubilizate of the disclosure in a more simple and convenient way for the consumer or patient, the disclosure also provides a capsule filled with a solubilizate as described above, wherein the capsule is in the form of a soft gelatin capsule or a hard gelatin capsule or a soft gelatin-free capsule or a hard gelatin-free capsule, for example a cellulose capsule.

Moreover, in the context of the disclosure, the solubilizate according to the disclosure may be incorporated into other fluids, in particular liquids. The active substance-filled small micelles will be retained when doing so. Thus, the disclosure also provides a fluid containing the solubilizate as described above, wherein the fluid is selected from the group consisting of foods, dietary supplements, beverages, cosmetics, and pharmaceutical products. In the context of the disclosure, the fluid may in particular comprise an aqueous dilution of the solubilizate.

The disclosure furthermore provides a method for treating and/or preventing diseases involving inflammation, cancer, Alzheimer's, Parkinson's, obesity, high cholesterol, elevated blood sugar, diabetes, metabolic syndrome, and/or autoimmune diseases, multiple sclerosis (MS), for reducing visceral fat, for thermogenesis, for lowering cholesterol, in particular LDL cholesterol, and/or glucose in the blood and/or triglycerides in the blood, for improving macular pigment density, for reducing oxidative stress and/or for reducing the accumulation of fat in the hepatocytes, in particular as a pharmaceutical drug for treating and/or preventing fatty liver disease, Friedreich's ataxia, lysosomal diseases, in particular Tay-Sachs disease, arteriosclerosis, heart diseases, arthritis, for improving macular pigment density, wherein the method comprises administering to the dietary supplement consumer or patient a solubilizate according to the disclosure, in particular in a capsule or as a fluid, in particular orally, in particular once a day.

In a preferred embodiment of the inventive method, the solubilizate is administered to the dietary supplement consumer or patient in a curcumin dose ranging from 0.5 mg/kg body weight to 1 mg/kg body weight, preferably in a dose of 0.81 mg/kg body weight.

In a preferred embodiment of the inventive method, the solubilizate is administered to the dietary supplement consumer or patient in a *Boswellia* dose ranging from 1 mg/kg body weight to 2 mg/kg body weight, preferably in a dose of 1.62 mg/kg body weight.

In a preferred embodiment of the inventive method, the solubilizate is administered to the dietary supplement consumer or patient in a xanthohumol dose ranging from 0.5 mg/kg body weight to 1 mg/kg body weight, preferably in a dose of 0.81 mg/kg body weight.

For producing a solubilizate according to the disclosure comprising curcumin and at least one further active substance, it is possible to either mix together individually prepared solubilizates, or to directly prepare a solubilizate containing curcumin and at least one further active substance.

The disclosure furthermore provides methods for producing a solubilizate as described above. If co-micellization of curcumin and at least one further active substance is desired, the disclosure provides the following first variant of a preparation method, comprising the steps of
  (a) providing polysorbate 80 and/or polysorbate 20 and/or a mixture of polysorbate 20 and polysorbate 80;
  (b) adding at least one further active substance, in particular *Boswellia serrata* extract and/or xanthohumol;
  (c) adding curcumin powder;
  wherein step (a) comprises heating to a temperature in the range from 40° C. to 62° C., preferably to a temperature in the range from 45° C. to 57° C., most preferably to a temperature in the range from 48° C. to 52° C.; and
  wherein step (b) comprises keeping the temperature unchanged compared to step a), or heating to a temperature in the range from 60° C. to 75° C., preferably to a temperature in the range from 61° C. to 70° C., most preferably to a temperature in the range from 63° C. to 67° C.; and
  wherein step (c) comprises heating to a temperature in the range from 82° C. to 97° C., preferably to a temperature in the range from 83° C. to 92° C., most preferably to a temperature in the range from 85° C. to 89° C.

This preparation method allows to produce a solubilizate which is able to form micelles loaded with curcumin and with at least one further active substance, in an aqueous dilution. For this purpose, it is also possible to mix the at least two active substances with one another in a preparatory step under appropriately adapted temperature control, and then to add them in combined form, as a mixture.

In particular it is possible, prior to step b), to performed a step
  b1) comprising adding water at a temperature in the range from 40° C. to 62° C., preferably at a temperature in the range from 45° C. to 57° C., most preferably at a temperature in the range from 48° C. to 52° C.

Additionally or alternatively, step b1) may comprise adding ethanol at a temperature in the range from 40° C. to 62° C., preferably at a temperature in the range from 45° C. to 57° C., most preferably at a temperature in the range from 48° C. to 52° C.

Another option for a preparation method involving co-micellization of curcumin and at least one further active substance is provided by the following second variant of the disclosure with a method comprising the steps of
  (a) preparing a first preparation by providing polysorbate 80 and/or polysorbate 20 and/or a mixture of polysorbate 20 and polysorbate 80 and at least a first active substance, in particular α-lipoic acid;
  (b) preparing a second preparation by providing water and at least one further active substance, in particular serrapeptase;
  (c) adding at least one further active substance, in particular xanthohumol and/or *Boswellia serrata* extract and/or glavonoid and/or resveratrol and/or coenzyme $Q_{10}$, and adding curcumin powder to the second preparation from step (b);
  (d) combining the first preparation from step (a) and the second preparation from step c);
  wherein the temperature is in the range from 18° C. to 22° C. during the execution of steps (a) through (d);
  (e) heating to a temperature in the range from 80° C. to 97° C., preferably to a temperature in the range from 83° C. to 92° C., most preferably to a temperature in the range from 85° C. to 89° C.

Step c) may further comprise adding ethanol and/or glycerol and/or MCT oil and/or polysorbate 20 and/or polysorbate 80 and/or a mixture of polysorbate 20 and polysorbate 80.

A further option for a preparation method involving co-micellization of curcumin and at least one further active substance is provided by the following third variant of the disclosure with a method comprising the steps of
- (a) providing polysorbate 80 and/or polysorbate 20 and/or a mixture of polysorbate 20 and polysorbate 80 and of glycerol and of ethanol;
- (b) adding at least one further active substance, in particular an ethanolic extract of hard resins from hops, in particular Xantho-Flav Pure powder;
wherein step (a) comprises heating to a temperature in the range from 40° C. to 62° C., preferably to a temperature in the range from 45° C. to 57° C., most preferably to a temperature in the range from 48° C. to 52° C.;
and wherein step (b) comprises heating to a temperature in the range from 60° C. to 75° C., preferably to a temperature in the range from 61° C. to 70° C., most preferably to a temperature in the range from 63° C. to 67° C.; and
- (c) adding curcumin powder at a temperature in the range from 70° C. to 92° C., preferably at a temperature in the range from 75° C. to 87° C., most preferably at a temperature in the range from 78° C. to 82° C.;
- (d) adding glavonoid under heating to a temperature in the range from 80° C. to 97° C., preferably to a temperature in the range from 83° C. to 92° C., most preferably to a temperature in the range from 85° C. to 89° C.

The disclosure also relates to solubilizates which exhibit micelles in aqueous dilution loaded with curcumin alone or else with another active substance alone, at least immediately after their preparation. Therefore, the disclosure also provides a method for producing a solubilizate as described above by mixing a curcumin solubilizate and a solubilizate of at least one further active substance, in particular in a quantitative ratio of 1:1 of the individual solubilizates.

The disclosure will now be explained in more detail by way of exemplary embodiments. The following components were used:

Curcumin

The product named "Turmeric Oleoresin Curcumin Powder 95%" with the product code EP-5001 from Green Leaf Extraction Pvt Ltd., Kerala, India, was used as the curcumin. The curcumin powder has CAS Number 458-37-7. It is a natural product obtained by solvent extraction of the rhizomes of *Curcuma Longa*. The curcumin content of the powder is at least 95%, according to manufacturer specifications. This curcumin content is determined by ASTA method 18.0.

As an alternative to the "oleoresin turmeric 95%" curcumin powder from Green Leaf mentioned above, it is also possible for the exemplary embodiments described below to use, as the curcumin, 95% curcumin extract by Neelam Phyto-Extracts, Mumbai, India, or curcumin BCM-95-SG or curcumin BCM-95-CG from eurochem GmbH, Gröbenzell, Germany, or *Curcuma* Oleoresin 95% from Henry Lamotte OILS GmbH, Bremen, Germany, for example.

*Boswellia*

In the context of the present application, the term "*Boswellia*" in particular refers to an extract from the resin of the frankincense plant. Specifically, an extract of the species *Boswellia serrata* was used, which was an extract obtained by extraction with ethyl acetate from the resin of the plant with the botanical name *Boswellia serrata* with the product code "HC22519" manufactured by Frutarom Belgium N. V., Londerzeel, Belgium. A solubilizate containing this extract is also referred to as "boswellic acid solubilizate" because of its content of boswellic acids.

Besides extracts from the resin of the frankincense plant, it is also possible to use boswellic acids and/or derivatives of boswellic acids for the purposes of the solubilizates according to the disclosure. In particular, the following may be considered: alpha-boswellic acid (CAS number 471-66-9), beta-boswellic acid (CAS number 631-69-6) and their derivatives, 3-O-acetyl-alpha-boswellic acid (CAS number 89913-60-0), 3-O-acetyl-beta-boswellic acid (CAS number 5968-70-7), 11-keto-beta-boswellic acid (KBA, CAS number 17019-92-0), and 3-O-acetyl-11-keto-beta-boswellic acid (AKBA, CAS number 67416-61-9).

Xanthohumol

The products "Xantho-Flav" or "Xantho-Flav Pure" of the brand "Hopsteiner" by Simon H. Steiner, Hopfen, GmbH, Mainburg, Germany were used as the xanthohumol source. Both are natural products produced from hops. The active substance is the hop polyphenol xanthohumol. This is a yellow colored powder with a xanthohumol content between 65% and 85% in "Xantho-Flav" and at least 85% in "Xantho-Flav Pure", according to manufacturer specifications.

The concentrations of xanthohumol and isoxanthohumol in "Xantho-Flav Pure" are quantified by the manufacturer according to UV spectrophotometric analysis or HPLC EBC 7.8 using external calibration standard pure XN (370 nm) or IX (290 nm). "Xantho-Flav Pure" contains the prenylated flavonoid xanthohumol in a very high concentration. For the exemplary embodiments in the context of the present application, "Xantho-Flav Pure" of batch number 9432 was used.

Glavonoid/Glabridin

"Glavonoid" is the product name for a composition of Kaneka Corporation, Osaka, Japan, which contains glabridin as an active substance. Glabridin is a flavonoid of the licorice plant (*Glycyrrhiza glabra*). The product "Kaneka Glavonoid" contains 30% of licorice extract and 70% of edible oil, according to the manufacturer. "Kaneka Glavonoid" is standardized to 3% glabridin, according to the manufacturer, which is the main component of the polyphenols of the licorice plant. The CAS number of glabridin is 59870-68-7.

Resveratrol

The product "eveResveratrol" was used as resveratrol. This is transresveratrol obtained by fermentation. The product is provided as a whitish powder without additives. The content of transresveratrol is at least 98 wt %, the rest is water. The product has CAS number 501-36-0 and product code RSXOL 9800.

Serrapeptase

The product named Serratiopeptidase from Shaanxi Pioneer Biotech Co. Ltd. with batch number PBD 20170708 was used as serrapeptase. This is a greyish white to light brown powder.

Coenzyme $Q_{10}$

Coenzyme $Q_{10}$ was purchased from Xiamen Kingdomway Group Company. It was produced by microbial fermentation and contains less than 0.5% of the cis isomer, according to the manufacturer's specifications.

α-Lipoic acid (alpha-liponic acid)

Alpha-lipoic acid was purchased from Jiangsu Tohope Pharmaceutical Co. Ltd., China.

Polysorbate 80

The source of polysorbate 80 was the material "TEGO SMO 80 V FOOD" with the specification code "K04 EU-FOOD" from Evonik Nutrition & Care GmbH, Essen, Germany. The product complies with the EU requirements for food additive E 433. As an alternative to the TEGO SMO 80 V from Evonik mentioned above, it is also possible to use TEGO SMO 80 V from InCoPA Gmbh, Illertissen, Germany, or Crillet 4/Tween 80-LQ-(SG) from CRODA GmbH, Nettetal, Germany, or Lamesorb SMO 20 and Kotilen-O/1 VL from Univar or from Kolb Distributions A G, Hedingen, Switzerland, as the polysorbate 80 in the exemplary embodiments described below.

Polysorbate 20

The source of polysorbate 20 was the material "TEGO SML 20 V FOOD" with the specification code "K09 EU-FOOD" from Evonik Nutrition & Care GmbH, Essen, Germany. The product complies with the EU requirements for food additive E 432. As an alternative to the TEGO SML 20 from Evonik mentioned above, it is also possible to use Crillet 1/Tween 20-LQ-(SG) from CRODA GmbH, Nettetal, Germany, as the polysorbate 20 within the context of the disclosure.

Ethanol

In the context of the present application, ethanol was purchased from Berkel Pfälzische Spritfabrik GmbH & Co. KG. According to the specification for "undenatured neutral alcohol 1411U taxed", the content of ethanol of this product is about 92.6 to 95.2 wt %.

Glycerol

The product used as glycerol in the context of the present application was "Glycamed 99.7%" from Glaconchemie GmbH, Merseburg, Germany. The glycerol content of this product is at least 99.5%, according to manufacturer specifications.

Medium-Chain Triglycerides

Medium-chain triglycerides (MCTs) are triglycerides that contain medium-chain fatty acids. Medium-chain fatty acids include caproic acid, caprylic acid, capric acid and lauric acid. These are saturated fatty acids which naturally occur in tropical vegetable fats such as coconut oil and palm kernel oil. To a small extent they are also contained in milk fat. There is no pure MCT oil in nature, however, pure MCT oils can be obtained synthetically. Individual MCTs or a mixture of different MCTs can be used as medium-chain triglycerides within the scope of the disclosure. Medium-chain triglycerides were used in the form of MCT oil Delios VK Kosher, manufactured by Cognis GmbH, Monheim, Germany, or in the form of MCT oil (70/30) Rofetan GTCC 70/30 manufactured by DHW Deutsche Hydrierwerke Rodleben GmbH, Dessau-Roßlau, Germany, CAS number 73-398-61-5.

Furthermore, medium-chain triglycerides can be used in the form of the product ROFETAN DTCC 70/30 (Ph. Eur.). This is a caprylic/capric acid triglyceride with CAS number 73398-61-5. The product corresponds to the monograph "medium-chain triglycerides" of the European Pharmacopoeia valid at the filing date. Manufacturers are Ecogreen Oleochemicals DHW, Deutsche Hydrierwerke GmbH, Rodleben, Germany.

Mixed Tocopherol

The 70% mixed tocopherol in vegetable oil Vitapherole T-70 Non GMO, manufactured by VitaeNaturals can be used as a mixed tocopherol (E306, CAS numbers 59-02-9, 16698-35-4, 54-28-4, and 119-13-1), for example.

If water is added in the preparation of a solubilizate, distilled water is used.

Prof. Dr. Ing. M. T. Khayyal from the University of Cairo, Faculty of Pharmacy at the Institute for Pharmacology, performed studies on the anti-inflammatory effect of curcumin and combinations of curcumin with *Boswellia* or xanthohumol, in each case in the native form and in the solubilized form according to the disclosure.

Anti-inflammatory markers and antioxidant capacity were determined. Female Wistar rats with a body weight between 150 and 200 g were exposed to adjuvant induced arthritis according to Pearson et al. (1956). At day 0, the animals were administered 0.1 ml of Freund's Adjuvant (FCA) in the right hind paw, by subplantar injection. The animals were randomly divided into 12 groups of 8 animals each.

Group 1 was the control group.

Group 2 received diclofenac as a reference drug in a dose of 3 mg/kg body weight.

Group 3 received native curcumin in a dose of 5 mg/kg body weight.

Group 4 received curcumin solubilized according to the disclosure in a dose of 5 mg/kg body weight.

Group 5 received native curcumin in a dose of 10 mg/kg body weight, and

Group 6 received curcumin solubilized in the same dose.

Group 7 received native xanthohumol in a dose of 5 mg/kg body weight, and

Group 8 received solubilized xanthohumol in the same dose.

Group 9 received a mixture of native curcumin in a dose of 5 mg/kg body weight and native *Boswellia* extract in a dose of 10 mg/kg body weight.

Group 10 received a mixture of solubilized curcumin and solubilized *Boswellia* in the same respective dose.

Group 11 received a mixture of native curcumin in a dose of 5 mg/kg body weight and native xanthohumol in a dose of 5 mg/kg body weight, and Group 12 received a mixture of solubilized curcumin and solubilized xanthohumol in the same respective dose.

All extracts or solubilizates were administered orally once daily from day 0 to day 21 following the vaccination with the adjuvant. After day 21, the animals were killed and serum samples were prepared and stored at −80° C. Measurements were made of myeloperoxidase (MPO), C-reactive protein (CRP), total antioxidant capacity (TAC), and thiobarbituratic acid reactive substances (TBARS).

BRIEF DESCRIPTION OF THE DRAWINGS

The results will now be explained with reference to the accompanying figures, wherein.

DETAILED DESCRIPTION

Figure 1A:
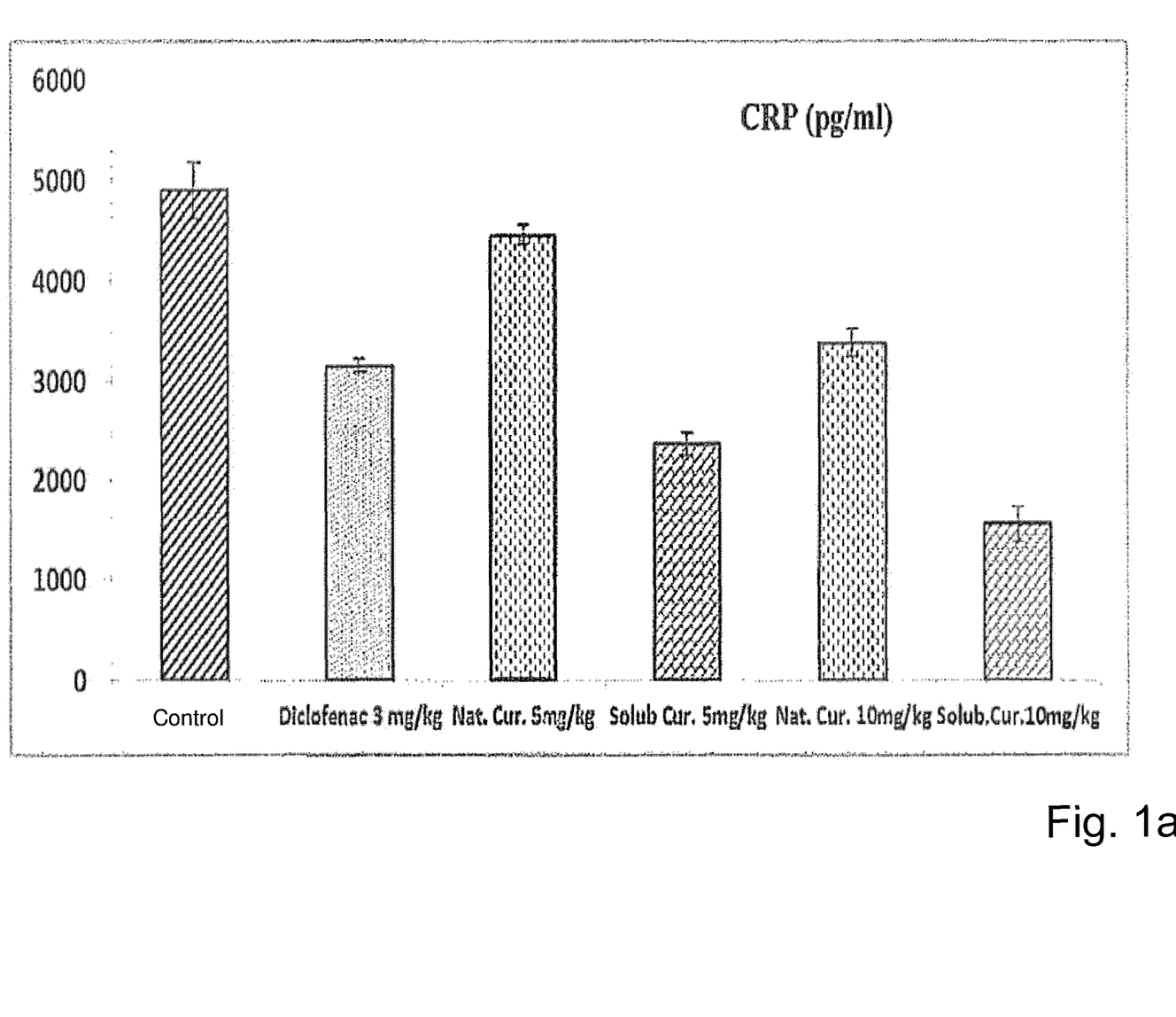
FIG. 1a illustrates the effect of curcumin in native and in solubilized form and of diclofenac on the serum CRP level (pg/L).

First, the effects on C-reactive protein (CRP) were studied. C-reactive protein is a specific marker for anti-inflammatory activity. Both the native and the solubilized forms of curcumin inhibited rat serum CRP levels in a dose-dependent manner, but the solubilized form was twice as effective as the native form and significantly more effective than diclofenac at the chosen dose (FIG. 1a).

Figure 1B:
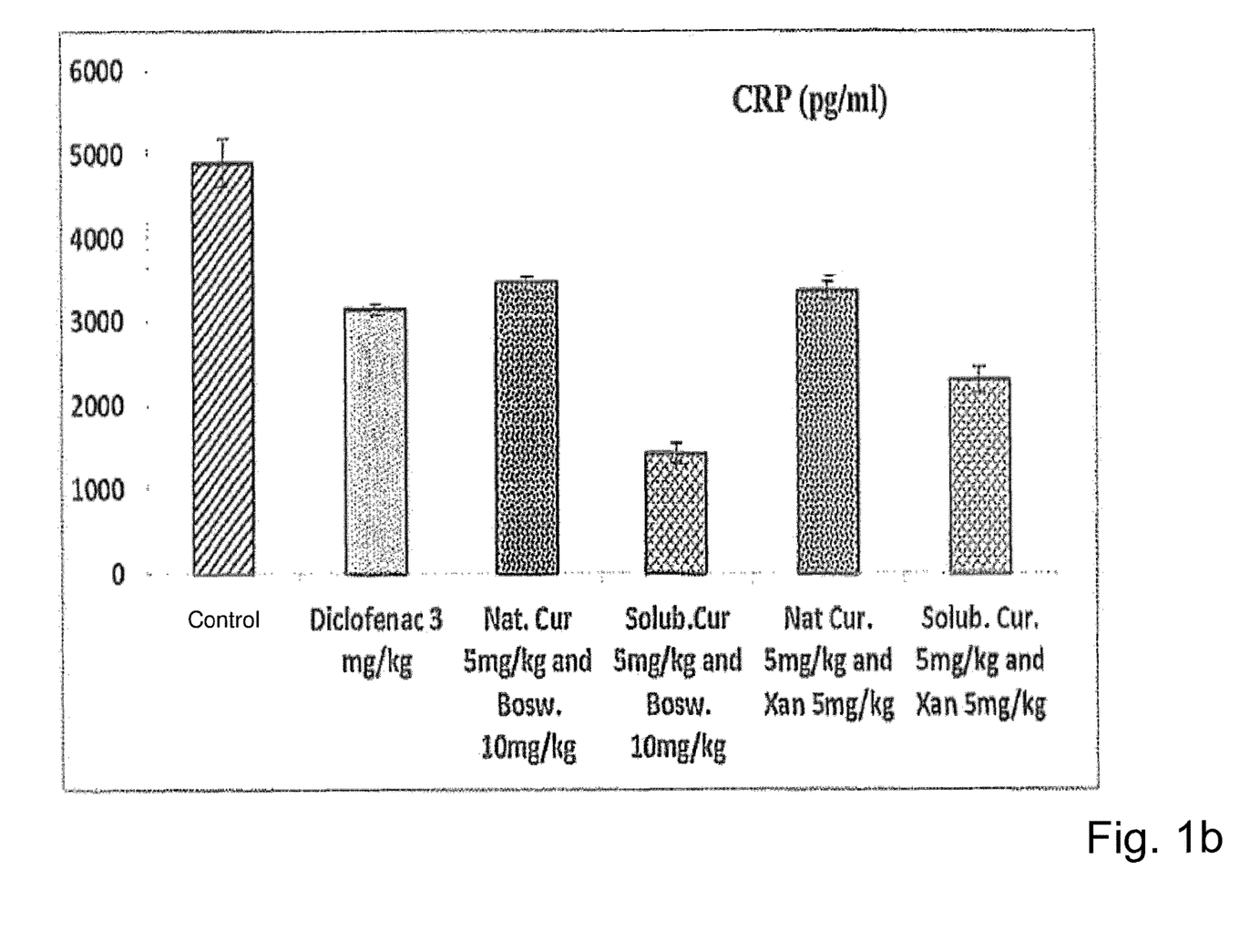
FIG. 1b illustrates the effect of curcumin (5 mg/mL) in native and in solubilized form when administered together with either *Boswellia* or xanthohumol on the serum CRP level (pg/L), compared to diclofenac.

When *Boswellia* is administered together with curcumin in their native forms, the inhibitory effect on serum CRP does not change significantly (FIG. 1b). However, when curcumin and *Boswellia* are administered in solubilized form together and at an appropriate dose, the anti-inflammatory effect is enhanced. In this regard, *Boswellia* is superior to xanthohumol in potentiating the effect of curcumin at the considered doses.

Figure 2:
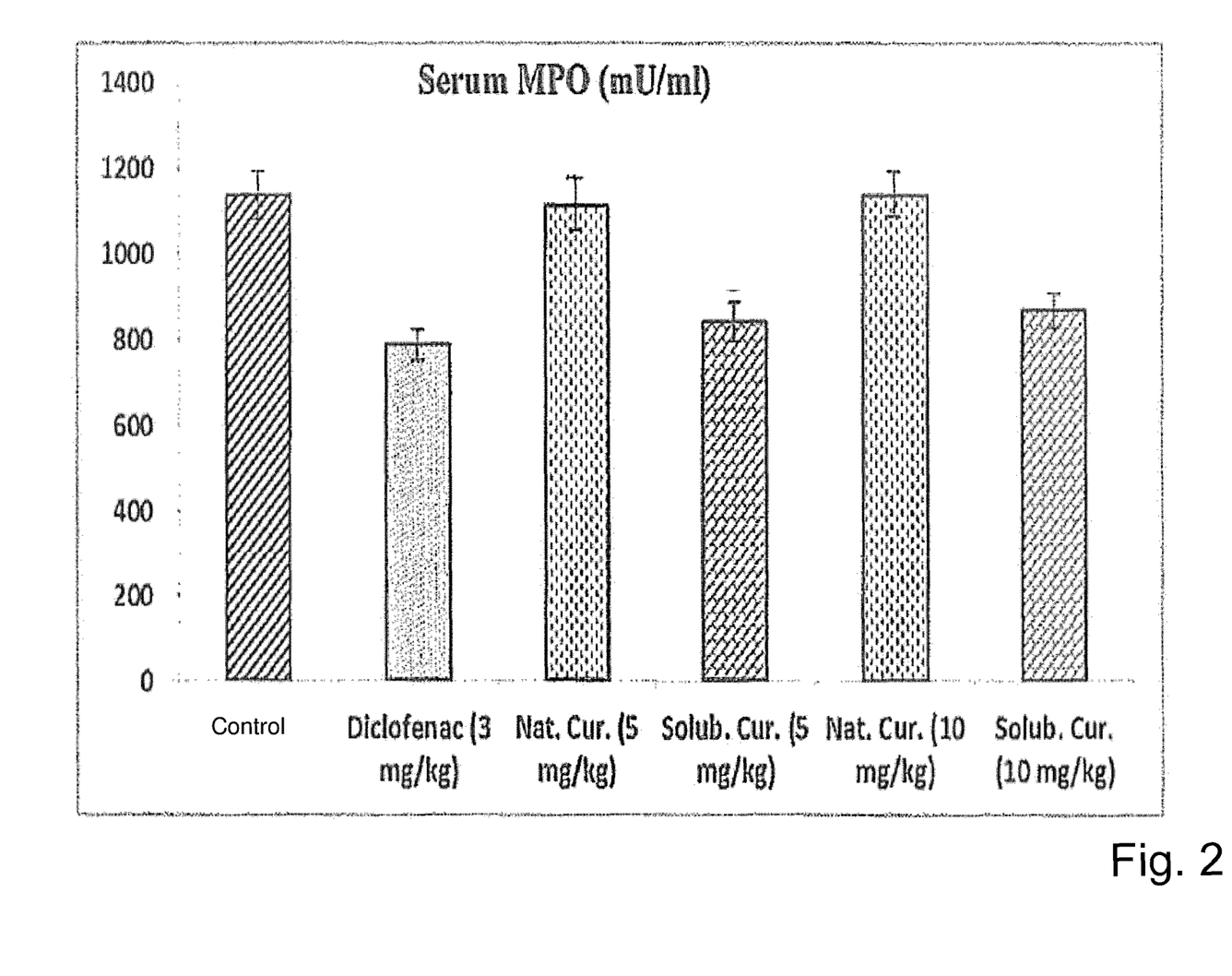
FIG. 2 illustrates the effect of curcumin in native and in solubilized form and of diclofenac on the serum MPO level (mU/mL).
Figure 3:
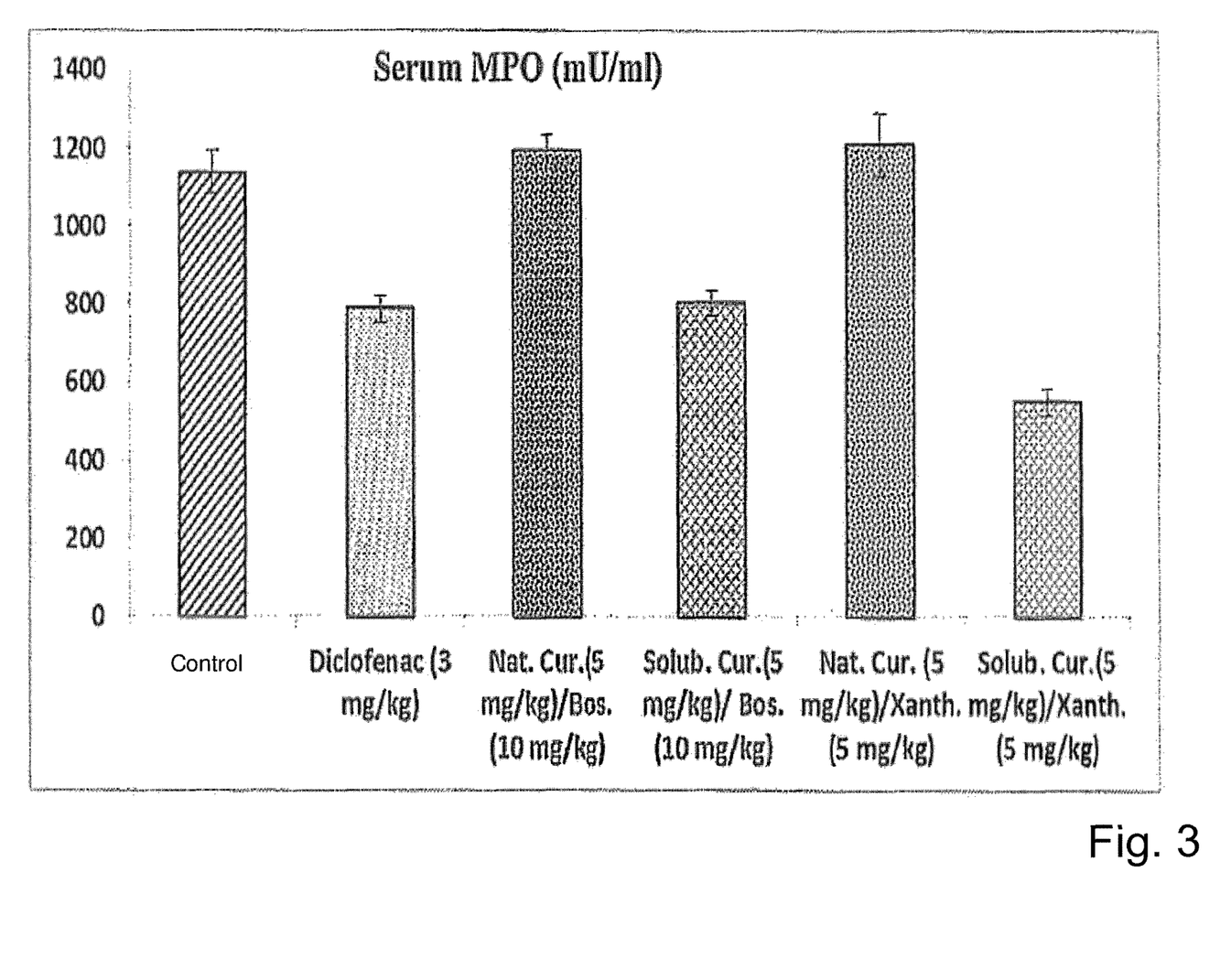
FIG. 3 illustrates the effect of curcumin in native and in solubilized form when administered together with either *Boswellia* or xanthohumol on the serum MPO level (mU/mL), compared to diclofenac.

Myeloperoxidase (MPO) in plasma plays a central role as a pro-inflammatory mediator in rheumatoid arthritis and is an indicator of the invasion of neutrophil granulocytes into the affected tissue. Its concentration is elevated in patients with rheumatoid arthritis and causes oxidative stress. In the studies, the MPO concentration was effectively reduced by solubilized curcumin, at both dosages considered in the same way and not significantly different from diclofenac. However, native curcumin had no effect on the MPO levels (FIG. 2). The administration of *Boswellia* together with curcumin, both in the native and the solubilized forms, did not improve the effect of curcumin in reducing MPO levels.

Oxidative stress is one of the major factors contributing to joint destruction in rheumatoid arthritis (RA). An increase in the production of so-called "reactive oxygen species (ROS)" leads to a reduced supply of endogenous antioxidants and ultimately results in the destruction of cells. The neutrophil granulocytes released in the rheumatoid joint produce free oxygen radicals which cause increased formation of lipid peroxides manifesting in an increase in serum TBARS. Therefore, an increase in antioxidant status represented by an increase in TAC can be used as an indication of protection against the development of degenerative inflammatory processes. There is an inverse relationship between the levels of TAC and TBARS, a high level of antioxidant capacity TAC corresponds to a low TBARS concentration.

The studies that were performed showed that, at both dosages considered, the native form of curcumin had no significant effect on the levels of TBARS or TAC. Solubilized curcumin according to the disclosure reduced the TBARS level at both selected dosages and increased TAC, with hardly any differences to the effect of diclofenac.

These data are summarized in the table below. The table contains data on the effect of curcumin and *Boswellia* in native and in solubilized form, administered either alone or in combination with diclofenac in a dose of 3 mg per kg body weight once daily for 21 days, on the antioxidant capacity TAC and the thiobarbituric acid reactive substances TBARS in the serum of arthritic rats (n=8). Indicated are mean values ±standard error of the mean (SEM).

| Group | TAC (nmol/microliter) | TBARS (nmol/L) |
| --- | --- | --- |
| Arthritic control group | 57.26 ± 3.36 | 13.10 ± 0.39 |
| Diclofenac (3 mg/kg) | 82.08 ± 2.96 | 7.93 ± 0.84 |
| Native curcumin (5 mg/kg) | 60.31 ± 3.25 | 11.64 ± 0.39 |
| Solubilized curcumin (5 mg/kg) | 77.01 ± 0.73 | 5.97 ± 0.47 |
| Native curcumin (10 mg/kg) | 68.41 ± 1.09 | 13.18 ± 0.46 |
| Solubilized curcumin (10 mg/kg) | 87.15 ± 5.27 | 6.82 ± 0.56 |
| Native curcumin (5 mg/kg) + Boswellia (10 mg/kg) | 64.56 ± 1.45 | 12.08 ± 0.52 |
| Solubilized curcumin (5 mg/kg) + Boswellia (10 mg/kg) | 76.94 ± 2.17 | 6.81 ± 0.19 |

According to the results presented in the table, the administration of *Boswellia* together with curcumin, each in native form, did not show any significant effect for reducing the oxidative stress. In solubilized form, however, these combinations were as effective as diclofenac in reducing TBARS and increasing TAC in arthritic rat's serum.

First studies on the use of the curcumin solubilizate according to the present disclosure in combating cancer cells of the lines (MCF-7) and (T47D) for breast cancer, (Hepg-2) for liver cancer, (HCT-116) for colon cancer, and (PC3) for prostate cancer show very good results in terms of achieving the lowest possible proportion of cells that survive the treatment. The curcumin solubilizate permitted a reduction to a "surviving fraction" in the range from about 15% to about 25%.

The particle size analyzes of the micelles in aqueous dilutions of solubilizates according to the disclosure were measured according to the principle of dynamic light scattering using laser light of 780 nm wavelength, unless stated otherwise. The particle size measurements were performed using the ParticleMetrix NANO-flex backscatter particle analyzer. The measuring principle is based on dynamic light scattering (DLS) in a 180° heterodyne backscattering setup.

For the experimental determination of turbidity of the solubilizates according to the disclosure, the turbidity meters are calibrated with a standard suspension. Thus, instead of measured light intensity, the concentration of the calibration suspension is indicated. So, when any arbitrary suspension is measured, the indication means that the respective liquid causes the same light scattering as the standard suspension at the indicated concentration. The internationally defined turbidity standard is formazine. The most common units include the indication FNU, i.e. Formazin Nephelometric Units. This is the unit used in water treatment, for example, for measuring at 90° in compliance with the requirements of the ISO 7072 standard.

For preparing a solubilizate according to the disclosure including the active substances curcumin and at least one further active substance it is possible to either mix individually prepared solubilizates with one another or to directly prepare a solubilizate containing curcumin and at least one further active substance or several further active substances.

Curcumin Solubilizates

By way of example, a 7% curcumin solubilizate is prepared. To this end, 925 g polysorbate 80 and 75 g curcumin powder 95% (=71.2 g of curcumin)

are used. The polysorbate 80 is heated to 48 to 52° C. The curcumin powder is added to the polysorbate under stirring, while further heating to a temperature in the range from 95 to 97° C. The powder is added at an appropriate rate so as to be evenly drawn into the emulsifier during stirring. After cooling to a temperature below a maximum of 60° C., the curcumin solubilizate is bottled. This solubilizate was used for the preparation of a curcumin and *Boswellia* solubilizate.

At a 1:500 dilution in water at pH 1.1 and a temperature of 37° C., the 7% curcumin solubilizate exhibits an average turbidity of 0.9 FNU.

However, it should be noted that the curcumin content can be further increased without having to accept adverse consequences, for example in terms of stability of the micelles. A composition consisting of 100 g of 95% curcumin powder and 900 g of polysorbate 80 results in a stable product just like a composition consisting of 120 g of 95% curcumin powder and 880 g of polysorbate 80, or 70 g of 95% curcumin powder and 930 g of polysorbate 80.

Moreover, the polysorbate 80 may be entirely or partially replaced by polysorbate 20. For example, for preparing a curcumin solubilizate with polysorbate 20 alone, 894 g of polysorbate 20 and 106 g of 95% curcumin powder can be used. The polysorbate 20 is heated to between about 63° C. and about 67° C. While stirring, the curcumin powder is slowly added to the polysorbate 20. While adding the curcumin powder, heating is continued to between about 83° C. and about 87° ° C. The resulting solubilizate is slowly cooled to below about 45° C. and is then ready for being bottled.

Otherwise, the preparation of these variants corresponds to that described above. Solubilizates of up to about 11% can be produced in this way.

1.5% Serrapeptase Solubilizate

The following is used:
15 g serrapeptase: serratiopeptidase 20,000 U/mg=300,000,000 U,
15 g water,
16.5 g MCT oil,
953.5 g polysorbate 80.

At a temperature in the range between 18 and 22° C., water is mixed with serrapeptase, and the mixture is homogenized. This means that the serrapeptase is distributed as evenly as possible in the water. This creates the conditions for the serrapeptase to be largely completely dissolved in the water. While heating to a temperature in the range from 83 to 87° C., MCT oil is incorporated into the water-serrapeptase mixture under constant stirring. The stirring is performed intensely enough for the serrapeptase to dissolve evenly in the water. At unchanged temperature, polysorbate 80 is added under stirring and is homogenized. The stirring is performed intensely enough for the polysorbate 80 to be evenly distributed. The product is cooled to a temperature below 60° C. and bottled. It is then stored in the dark at not more than 25° C.

300,000 U/g corresponds to 15 mg/g of 1.5% serrapeptase in enzymatic units. At a dilution in water of 1:50, the turbidity of this solubilizate was determined under physiological conditions at pH 1.1 and 37° C. The resulting value was 1.8 FNU.

For a particle size analysis of the serrapeptase solubilizate, this solubilizate was first diluted with distilled water in a ratio of 1:500 and heated to 37° C. under constant stirring using a magnetic stirrer and a hotplate. Subsequently, the pH was adjusted to 1.1 using 32% hydrochloric acid. The samples were then measured immediately. The results are summarized in the table below, for which the data of two measurements were averaged.

|  | $d_{10}$ (nm) | $d_{50}$ (nm) | $d_{90}$ (nm) | $d_{99}$ (nm) |
| --- | --- | --- | --- | --- |
| Intensity distribution | 9.23 | 10.47 | 12.23 | 13.56 |
| Volume distribution | 9.10 | 10.18 | 11.82 | 13.12 |

10% Resveratrol Solubilizate

The following is used:
100 g resveratrol,
45 g MCT oil,
600 g polysorbate 80,
180 g polysorbate 20, and
75 g mixed tocopherol.

At a temperature in the range between 18 and 22° C., the polysorbates, the mixed tocopherol and the MCT oil are mixed and homogenized while stirring sufficiently so that the components are evenly distributed. The resveratrol is added to the mixture or solution of polysorbate, MCT oil and mixed tocopherol while heating to a temperature in the range from 83 to 87° C., while stirring sufficiently so that the resveratrol is evenly drawn into the emulsifier-containing preparation. Once a homogeneous and transparent product is obtained, it is cooled to a temperature below 30° C. and bottled. The product is yellowish, transparent and viscous and is stored in the dark at a temperature of 25° C.

If, for therapeutic purposes, the administration of 3,500 mg of the native form of the resveratrol raw material is taken as a basis, the following calculation applies to the equivalent amount of solubilizate:

3 capsule fillings, each with 675 mg of solubilizate, correspond to an amount of 2,025 mg per day or 200 mg of the active substance resveratrol and 100 mg of mixed tocopherol. With a DV factor of 1:17 the following applies: 200 mg×17=3,400 mg of resveratrol pure substance.

Turbidity of this solubilizate was also determined under physiological conditions (pH 1.1; 37° C.) at a dilution in water of 1:50. The resulting value was 16.1 FNU.

5% Coenzyme $Q_{10}$ solubilizate

The following is used:
57.5 g coenzyme $Q_{10}$,
160 g MCT oil, and
782.5 g polysorbate 80.

The polysorbate is heated to a temperature in the range between 83° C. and 87° C. Then the coenzyme $Q_{10}$ powder is incorporated under stirring. Stirring is performed intensely enough so that the components are evenly distributed. While maintaining the temperature or reheating to a temperature in the range from 83 to 87° C., the coenzyme $Q_{10}$ is dissolved in the polysorbate 80. Then, the MCT oil is incorporated while maintaining the temperature. Once a homogeneous and transparent product is obtained, it is cooled to a temperature below 60° C. and bottled. The product is orange-red, transparent and partially solid at room temperature. It is stored in the dark at a temperature of 25° C.

The measurement of turbidity under physiological conditions (pH 1.1; 37° C.) at a dilution in water of 1:50 gave a value of 11.9 FNU as the mean value of three measurements (11.4 FNU; 10.5 FNU; 13.9 FNU).

A particle size analysis of a sample of 20 microliters in a dilution ratio of 1:50 in a solution of table salt (50 mmol/L) and sodium azide (200 mg/L) by Wyatt Technology Europe GmbH in the Eclipse program, i.e. by field flow fractionation, gave a peak with a radius of 16.5 nm for the micelles of this solubilizate. Accordingly, the diameter of the micelles is 33 nm.

10% α-Liponic Acid Solubilizate

The following is used:
896.7 g polysorbate 80,
103.3 g α-lipoic acid.

The polysorbate 80 is heated to between 28 and 32° C. Under stirring, the α-lipoic acid powder is added to the polysorbate and incorporated. The powder is added at such a rate that it is evenly drawn into the emulsifier during stirring. This is followed by heating up to a temperature in the range between 83° C. and 87° C. Once a homogeneous and transparent product is obtained, it is cooled to a temperature below 60° C. and bottled. The product is yellow and viscous and is stored in the dark at a temperature of 25° C.

The product can also be produced using polysorbate 20 or a mixture of polysorbate 80 and polysorbate 20.

At a dilution ration of 1:50 in water at pH 1.1 and a temperature of 37° C., the solubilizate exhibits an averaged turbidity of 2.9 FNU.

A particle size analysis of a sample of 20 microliters in a dilution ratio of 1:50 in a solution of table salt (50 mmol/L) and sodium azide (200 mg/L) by Wyatt Technology Europe GmbH in the Eclipse program, i.e. by field flow fractionation, gave a peak with a radius below 10 nm for the micelles of this solubilizate. Accordingly, the diameter of the micelles is not more than 20 nm.

10% Xantho-Flav Pure Solubilizate (Corresp. to 9.2% Xanthohumol) with Ethanol

For this variant of a xanthohumol solubilizate according to the disclosure, the following was used:
100 g Xantho-Flav Pure (≙92 g of xanthohumol),
150 g ethanol (96%) of neutral alcohol grade 1411U, and
750 g polysorbate 80.

First, the Xantho-Flav Pure powder is dissolved in ethanol while being heated to a temperature in the range between 48 and 52° C. A homogeneous solution is created. Polysorbate 80 is then added into the solution of Xantho-Flav Pure in ethanol while heating to between 83 and 87° C. The adding is done at a rate such that the two fluids homogenize well under stirring. The resulting solubilizate is cooled to below 60° C. and is bottled and stored in the dark and cool, i.e. at temperatures below 25° C. 15% Glavonoid solubilizate (=0.45% glabridin) with glycerol The following was used:
150 g glavoniod (=4.5 g glabridin),
100 g 99% glycerol,
750 g polysorbate 80.

First, glycerol and glavonoid were mixed and homogenized at a temperature in the range from 18 to 22° C. While heating up to 83-87° C., polysorbate 80 was added to the fluid consisting of glycerol and glavonoid, under stirring. The stirring was performed intensely enough so that a homogeneous solubilizate was obtained, which was allowed to cool to a maximum of 30° C. and bottled and then stored in the dark at a temperature below 25° C.

The solubilizates described above can be used to prepare the solubilizate according to the disclosure comprising curcumin and at least one further active substance by mixing. This will be described below with reference to exemplary embodiments 3, 5, 6, and 7.

Exemplary Embodiment 1

Solubilizate of 5.4% Curcumin/6.6% Boswellic Acid

This exemplary embodiment of the solubilizate according to the disclosure was prepared directly. The active substances were co-micellized. To this end, the following was used here:
82 g 80% *Boswellia serrata* extract (=65.6 g boswellic acid),
57 g 95% curcumin powder (=54.1 g of curcumin),
70 g water,
350 g polysorbate 20,
441 g polysorbate 80.

While heating to a temperature in the range from 48 to 52° ° C., polysorbate 20 and polysorbate 80 are homogenized with each other and thereby dissolved in each other under stirring. While maintaining the temperature, the emulsifier mixture is mixed with the water while stirring intensely enough so that the water and the ethanol are dissolved evenly in the emulsifier solution. At unchanged temperature, the *Boswellia serrata* extract is incorporated into the water-diluted emulsifier under stirring. The *Boswellia serrata* extract is added at a rate slow enough to be evenly drawn into the dilute emulsifier solution under stirring. Subsequently, the temperature is increased to a range between 63° C. and 67° C. under vigorous stirring. The curcumin powder is incorporated under stirring. The temperature is further increased to a value in the range between 85° C. and 89° C. while stirring intensely enough for the curcumin to be evenly distributed in the preparation and homogenized.

At a dilution ration of 1:500 in water at pH 1.1 and a temperature of 37° C., the solubilizate exhibits an averaged turbidity of 1.9 FNU.

In the context of the present application, a verification about whether the homogenization of the components to form a solubilizate according to the disclosure has been sufficiently completed in the preparation of any solubilizates is obtained by measurements of the clarity of the product, which indicates complete micellization, using a laser beam. Such a laser beam measurement may be performed, for example, by illuminating the sample using a commercially available laser pointer, in particular with a wavelength in the range between 650 nm and 1700 nm (spectral color red), and subsequent visual inspection of the illuminated or irradiated solubilizate. The verification is not achieved by sampling and thus outside the reaction vessel, but in the reaction vessel. The laser beam is directed through a sight glass which is located on the front of the reaction vessel, perpendicularly to the reaction vessel. If merely a point of light appears on the rear inner surface of the reaction vessel, completely free of scattering, the resulting particle structures in the reaction vessel are smaller than the wavelength of the visible light, which is thus a visual confirmation that the process of micellization has been completed.

In the context of the disclosure, the contents of curcumin and *Boswellia* extract in the individual solubilizates may also be adjusted so as to be significantly higher than in the example shown, depending on the application case.

Exemplary Embodiment 2

Solubilizate of 3.3% Curcumin/3.6% Boswellic Acid with 1.8% Xanthohumol

The following is used:
45 g 80% *Boswellia serrata* extract (36 g boswellic acid),
35 g 95% curcumin powder (33.25 g of curcumin),
23 g Xantho-Flav with at least 80% xanthohumol (18.4 g xanthohumol),
60 g water,
50 g ethanol (96%) neutral alcohol, grade 1411U,
350 g polysorbate 20,
437 g polysorbate 80.

While heating to a temperature in the range from 48 to 52° C., polysorbate 20 and polysorbate 80 are homogenized with each other while being dissolved in each other, under stirring. While maintaining the temperature, the emulsifier mixture is mixed with the water and ethanol. Stirring is performed intensely enough so that the water and the ethanol are dissolved evenly in the emulsifier solution. At unchanged temperature, the *Boswellia serrata* extract and the xanthohumol are incorporated into the water-diluted emulsifier mixture while stirring. The adding occurs at a rate slow enough so that the *Boswellia serrata* extract and the xanthohumol are evenly drawn into the dilute emulsifier solution, under stirring. Subsequently, the temperature is increased to a range between 63° C. and 67° C. under vigorous stirring. The curcumin powder is incorporated while stirring. The temperature is further increased to a value in the range between 85° C. and 89° C. while stirring intensely enough so that the curcumin is evenly distributed in the preparation and homogenized.

This is followed by cooling to a temperature of less than or equal to 45° C. The dark yellow, viscous preparation comprising a solubilizate of curcumin and boswellic acid and xanthohumol is then bottled and stored in the dark and cool, i.e. below 25° C.

At a dilution ratio of 1:500 in water at pH 1.1 and a temperature of 37° C., the solubilizate exhibits an averaged turbidity of 1.9 FNU.

For particle size analysis of a solubilizate according to the disclosure, unless stated otherwise, this solubilizate was first diluted with distilled water in a ratio of 1:500 and brought to 37° C. under constant stirring with a magnetic stirrer and using a hot plate. Subsequently, the pH was adjusted to 1.1 using 32% hydrochloric acid. The samples were then measured immediately. The results are summarized in the table below.

|  | $d_{10}$ (nm) | $d_{50}$ (nm) | $d_{90}$ (nm) | $d_{99}$ (nm) |
| --- | --- | --- | --- | --- |
| Intensity distribution | 10.18 | 15.70 | 533.0 | 3080 |
| Volume distribution | 7.90 | 10.96 | 15.21 | 20.37 |

Exemplary Embodiment 3

Solubilizate of 1.5% Curcumin/3% Boswellic Acid/2% Xanthohumol/0.35% Serrapeptase The following is used according to the formulations described above:
250 g 7% curcumin solubilizate,
250 g 12% Bowellia solubilizate,
250 g 9.2% xanthohumol solubilizate, and
250 g 1.5% serrapeptase solubilizate.

All four solubilizates can be heated to a temperature in the range from 50° C. to 60° C. to lower viscosity and thus enhancing flowability. Subsequently, they are mixed together by stirring. As soon as a homogeneous complete product is obtained, it is optionally cooled to a temperature below 60° C. and bottled.

Prior to further processing such as filling into capsules, it is favorable to again stir the product to homogenize it, and if necessary to heat it moderately, that is to a temperature of about 40° C. to 50° ° C. At a dilution ratio of 1:500 in water at a pH of 1.1 and a temperature of 37° C., the solubilizate exhibits an averaged turbidity of 1.0 FNU. The results of particle size analysis are summarized in the table below.

|  | $d_{10}$ (nm) | $d_{50}$ (nm) | $d_{90}$ (nm) | $d_{99}$ (nm) |
| --- | --- | --- | --- | --- |
| Intensity distribution | 9.08 | 15.64 | 292.7 | 615 |
| Volume distribution | 6.35 | 9.36 | 14.10 | 20.16 |

Exemplary Embodiment 4

Solubilizate of 5% Glavonoid (=1.8% Glabridin)/3% Curcumin/3.5% Xanthohumol

The following is used:
32 g 95% curcumin powder (=30.4 g of curcumin),
44 g Xantho-Flav Pure powder (=35.2 g of xanthohumol),
60 g Kaneka glavonoid (=1.8 g glabridin),
60 g 96% ethanol, neutral alcohol grade 1411U,
44 g 99.5% glycerol,
760 g polysorbate 80.

Polysorbate 80 and glycerol are mixed together under stirring while being heated to a temperature in the range from 48 to 52° C. to homogenize the mixture adequately. Ethanol is incorporated into the polysorbate-glycerol mixture while stirring intensely enough to form a homogeneous solution, while the temperature is kept constant. Then, xanthohumol is incorporated into the solution of polysorbate, glycerol, and ethanol, while the temperature is raised to a value between 63 and 67° C. under stirring intensely enough for the xanthohumol to combine homogeneously with the prepared solution.

Subsequently, curcumin powder is incorporated into the xanthohumol solubilizate, while the temperature is raised to a value in the range between 78 and 82° C. As with the xanthohumol and also with the incorporation of glavonoid described below, stirring is performed intensely enough so that the newly added component of the solubilizate combines homogeneously with the solubilized product in the prepared fluid. For the addition of glavonoid, the temperature is further increased to a value in the range between 85 and 98° C.

The product is a solubilizate with co-micellated curcumin, xanthohumol, and glavonoid. It is allowed to cool to a maximum value of 45° C. while stirring and is then bottled.

Exemplary Embodiment 5

Solubilizate of 1.5% curcumin/2% xanthohumol/3.5% glavonoid (0.1% glabridin)/1.2% coenzyme $Q_{10}$ The following is used according to the formulations described above:
250 g 7% curcumin solubilizate,
250 g 9.2% xanthohumol solubilizate,
250 g 15% glavonoid solubilizate, and
250 g 5% coenzyme $Q_{10}$ solubilizate.

All four solubilizates can be heated to a temperature in the range from 50° C. to 60° C. to lower viscosity and thus enhance flowability. Then, they are mixed together by stirring. Once a homogeneous complete product is obtained, it is optionally cooled to a temperature below 60° C. and bottled.

Prior to further processing such as filling into capsules, it is favorable to again stir the product to homogenize it, and if necessary to this end to heat it moderately, that is to a temperature of about 40° C. to 50° C.

The results of particle size analysis are summarized in the following table.

|  | $d_{10}$ (nm) | $d_{50}$ (nm) | $d_{90}$ (nm) | $d_{99}$ (nm) |
| --- | --- | --- | --- | --- |
| Intensity distribution | 8.22 | 10.88 | 14.80 | 450 |
| Volume distribution | 7.78 | 10.06 | 13.10 | 16.39 |

Exemplary Embodiment 6

Solubilizate of 1.3% curcumin/1.6% xanthohumol/3% glavonoid (0.09% glabridin)/1% coenzyme $Q_{10}$/2% α-liponic acid The following is used according to the formulations described above:
200 g 7% curcumin solubilizate,
200 g 9.2% xanthohumol solubilizate,
200 g 15% glavonoid solubilizate,
200 g 5% coenzyme $Q_{10}$ solubilizate, and
200 g 10% α-lipoic acid solubilizate.

All five solubilizates can be heated to a temperature in the range from 50° C. to 60° C. to lower viscosity and thus enhance flowability. Then, they are mixed together by stirring. Once a homogeneous complete product is obtained, it is optionally cooled to a temperature below 60° C. and bottled.

Prior to further processing such as filling into capsules, it is favorable to again stir the product to homogenize it, and if necessary to this end to heat it moderately, i.e. to a temperature of about 40° C. to 50° C.

The results of particle size analysis are summarized in the following table.

|  | $d_{10}$ (nm) | $d_{50}$ (nm) | $d_{90}$ (nm) | $d_{99}$ (nm) |
|---|---|---|---|---|
| Intensity distribution | 8.85 | 11.64 | 17.05 | 981 |
| Volume distribution | 7.16 | 9.41 | 12.36 | 15.43 |

Exemplary Embodiment 7

Solubilizate of 0.8% Curcumin/1.5% Boswellic Acid/1% Xanthohumol/1.8% Glavonoid (0.05% Glabridin)/0.18% Serrapeptase/1.2% Resveratrol/0.6% Coenzyme $Q_{10/1}$.2% α-Liponic Acid The following is used according to the formulations described above:
- 125 g 7% curcumin solubilizate,
- 125 g 12% *Boswellia* solubilizate,
- 125 g 9.2% xanthohumol solubilizate,
- 125 g 15% glavonoid solubilizate,
- 125 g 1.5% serrapeptase solubilizate,
- 125 g 10% resveratrol solubilizate,
- 125 g 5% coenzyme $Q_{10}$ solubilizate, and
- 125 g 10% α-lipoic acid solubilizate.

All eight solubilizates can be heated to a temperature in the range from 50° C. to 60° C. to lower viscosity and thus enhance flowability. Then, they are mixed together by stirring. Once a homogeneous complete product is obtained, it is optionally cooled to a temperature below 60° C. and bottled.

Prior to further processing such as filling into capsules, it is favorable to again stir the product to homogenize it, and if necessary to this end to heat it moderately, i.e. to a temperature of about 40° C. to 50° C.

At a dilution ratio of 1:50 in water at a pH of 1.1 and a temperature of 37° C., the solubilizate exhibits an averaged turbidity of 12.5 FNU.

The results of particle size analysis are summarized in the following table.

|  | $d_{10}$ (nm) | $d_{50}$ (nm) | $d_{90}$ (nm) | $d_{99}$ (nm) |
|---|---|---|---|---|
| Intensity distribution | 8.09 | 10.91 | 15.19 | 425 |
| Volume distribution | 6.90 | 9.26 | 12.37 | 15.71 |

Exemplary Embodiment 8

Solubilizate of 0.8% Curcumin/1.5% Boswellic Acids/1% Xanthohumol/1.8% Glavonoid (0.05% Glabridin)/0.18% Serrapeptase/1.2% Resveratrol/0.6% Coenzyme $Q_{10}$/1.2% α-Liponic Acid in Direct Preparation The following is used:
- 9.375 g 95% curcumin powder,
- 19 g *Boswellia Serrata* extract (15.2 boswellic acid),
- 12.5 g Xantho-Flav powder (at least 80% xanthohumol=10 g xanthohumol),
- 18.75 glavonoid (0.56 g glabridin),
- 1.875 g serrapeptase (37,500,000 U),
- 12.5 g resveratrol,
- 7.19 g coenzyme $Q_{10}$,
- 12.5 g α-lipoic acid,
- 7.875 g water,
- 18.75 g ethanol,
- 12.5 g glycerol,
- 9.375 g mixed tocopherol,
- 27.685 g MCT oil,
- 122.5 g polysorbate 20, and
- 707.225 g polysorbate 80.

Polysorbate 80 is mixed with α-lipoic acid at a temperature in the range between 18 and 22° C. while stirring intensely enough so that a homogeneous mixture is created. Separately, the serrapeptase is dissolved in water in the same manner, at a temperature in the range from 18 to 22° C. The further ingredients ethanol, xanthohumol, curcumin, *Boswellia*, glavonoid, resveratrol, coenzyme $Q_{10}$, mixed tocopherol, glycerol, MCT oil, and polysorbate 20 are slowly and successively added to the mixture or solution of serrapeptase and water under constant stirring while the temperature is still in the range between 18 and 22° C. Care is taken to ensure good mixing and homogeneity of the product. If appropriate, pauses are taken between the addition of a substance and the addition of the next substance. The adding and stirring is performed slowly enough so that the particular ingredient to be added is evenly incorporated into the preparation.

Next, both mixtures, i.e. the polysorbate 80 and the α-liponic acid preparations, and the remaining mixture of all other ingredients are mixed together and further stirred at a temperature in the range from 18 to 22° C. This creates a homogeneous pasty mass similar to a slurry, which is heated to a temperature in the range from 85° C. to 89° C. The heating is performed under constant stirring and slowly enough so that the heated slurry always remains mixed as homogeneously as possible. After cooling to a temperature below 60° C., the product is bottled. It is dark and viscous and is stored in the dark at temperatures of not more than 25° C. Prior to further processing such as filling into capsules, it is favorable to again stir the product to homogenize it and, if necessary to this end, to heat it moderately, i.e. to a temperature of about 40° ° C. to 50° C.

At a dilution ratio of 1:50 in water at a pH of 1.1 and a temperature of 37° C., the solubilizate exhibits a turbidity of 1.0 FNU.

The results of the particle size analysis are summarized in the following table.

|  | $d_{10}$ (nm) | $d_{50}$ (nm) | $d_{90}$ (nm) | $d_{99}$ (nm) |
|---|---|---|---|---|
| Intensity distribution | 8.66 | 11.01 | 14.58 | 220.4 |
| Volume distribution | 7.96 | 9.87 | 12.59 | 15.52 |

Exemplary Embodiment 9

Solubilizate of 3% Curcumin/3.2% Boswellic Acid/1.6% Xanthohumol/1% CBD Oil

The following is used:
- 40.5 g 80% *Boswellia serrata* extract (32.4% boswellic acid),
- 31.5 g 95% curcumin powder (29.925 g of curcumin),
- 20.7 g Xantho-Flav powder containing at least 80% of xanthohumol (16.5 g xanthohumol),
- 54 g water, 45 g ethanol,
315 g polysorbate 20,
483 g polysorbate 80,
10 g CBD oil: 30% cannabidiol.

Cannabidiol (CBD) is a barely psychoactive cannabinoid derived from the female hemp *Cannabis sativa* or *Cannabis indica*. A non-THC-free CBD oil was used, which means that it may contain traces of THC. Tetrahydrocannabinol (THC) is responsible for the psychedelic effects of hemp plants.

While heating to a temperature in the range from 48 to 52° C., polysorbate 20 and polysorbate 80 are homogenized with each other while being dissolved in each other, under stirring. While maintaining the temperature, the emulsifier mixture is mixed with the water and ethanol. Stirring is performed intensely enough so that the water and the ethanol are dissolved evenly in the emulsifier solution. At unchanged temperature, the *Boswellia serrata* extract and the xanthohumol are incorporated into the water-diluted emulsifier mixture while stirring. The adding occurs at a rate slow enough so that the *Boswellia serrata* extract and the xanthohumol are evenly drawn into the dilute emulsifier solution under stirring. Subsequently, the temperature is increased to a range between 63° C. and 67° C. under vigorous stirring. The curcumin powder is incorporated while stirring. The temperature is further increased to a value in the range between 85° C. and 89° C. while stirring intensely enough so that the curcumin is evenly distributed in the preparation and homogenized. Subsequently, the CBD oil is incorporated into the mixture while stirring intensely enough so that the CBD oil is evenly distributed in the preparation and homogenized.

This is followed by cooling to a temperature of less than or equal to 45° C. The dark-yellow viscous preparation comprising a solubilizate of curcumin and boswellic acid and xanthohumol and CBD oil is then bottled and stored in the dark and cool, i.e. below 25° C. The solubilizate and an aqueous solution thereof are stably homogeneous and just as soluble in crystal clear form as the solubilizate according to exemplary embodiment 2.

It will be apparent to a person skilled in the art that the invention is not limited to the examples described above, but rather can be varied in multiple ways. It is in particular possible for the features of the individually illustrated examples to be combined or swapped.

What is claimed is:

1. A solubilizate, comprising: xanthohumol; an alcohol; and polysorbate 80.

2. The solubilizate as in claim 1, wherein the alcohol is ethanol.

3. The solubilizate as in claim 2, wherein the ethanol is ethanol 96%.

4. The solubilizate as in claim 1, wherein the solubilizate comprises micelles, wherein the micelles have an average diameter between 5 nm and 40 nm.

5. The solubilizate as in claim 1, wherein the solubilizate comprises micelles, wherein the micelles have an average diameter between 5 nm and 20 nm.

6. The solubilizate as in claim 1, wherein the solubilizate comprises micelles, wherein the micelles have an average diameter between 7 nm and 10 nm.

* * * * *